United States Patent

Gigandet et al.

[11] Patent Number: 5,914,991
[45] Date of Patent: Jun. 22, 1999

[54] SYNCRONIZING A DATA ACQUISITION DEVICE WITH A HOST

[75] Inventors: Scott Gigandet, Groveland; John F. Sullivan, Beverly; Robert Addiss, Westford, all of Mass.

[73] Assignee: Siemens Medical Systems, Inc., Iselin, N.J.

[21] Appl. No.: 08/884,857

[22] Filed: Jun. 30, 1997

[51] Int. Cl.[6] .................................................. H04L 7/00
[52] U.S. Cl. ........................................................ 375/355
[58] Field of Search ..................................... 375/355, 354

[56] References Cited

U.S. PATENT DOCUMENTS

| 4,788,697 | 11/1988 | Bell et al. | 375/364 |
| 4,805,191 | 2/1989 | Burch et al. | 375/229 |
| 4,975,651 | 12/1990 | Hagiwara | 327/147 |
| 5,375,604 | 12/1994 | Kelly et al. | 600/484 |
| 5,442,656 | 8/1995 | Kaku et al. | 375/354 |
| 5,510,740 | 4/1996 | Farrell et al. | 327/142 |
| 5,588,029 | 12/1996 | Maturi et al. | 375/364 |
| 5,617,871 | 4/1997 | Burrows | 600/300 |
| 5,703,905 | 12/1997 | Langberg | 375/232 |
| 5,724,396 | 3/1998 | Claydon et al. | 375/355 |
| 5,790,613 | 8/1998 | Tateishi | 375/376 |

OTHER PUBLICATIONS

Application Note published by Actel Corporation in Apr. 1996 entitled "Using FGPAs for Digital PLL Applications".

*Primary Examiner*—Don N. Vo
*Assistant Examiner*—Lenny Jiang
*Attorney, Agent, or Firm*—Lawrence C. Edelman

[57] ABSTRACT

Apparatus for synchronizing a reference clock signal received from a host system with an A/D converter clock signal generated in a data acquisition pod. The pod includes a decoder responsive to communication received from the host for extracting a host reference signal, and a clock signal source for developing an A/D reference clock signal having a frequency that is different from the frequency of the host reference signal. A pulse modifying digital phase-locked loop (PLL) is responsive to the A/D reference clock signal and the host reference signal for developing an A/D clock signal for an A/D converter in which one of its clock periods is periodically modified, thereby locking the rate at which the A/D converter develops samples to the rate at which the host system requests samples. In a preferred embodiment the pod also includes a signal detector for detecting a specified alignment in time of the readiness of the A/D converter to provide a given sample with a host system request for that given sample, and upon such detection, selectively providing an enable signal to the PLL, thereby enabling operation of the PLL and synchronizing the host and pod clock rates, as well as locking in a given alignment the providing to the host of the samples developed by the A/D converter with the host system requests for those samples.

19 Claims, 3 Drawing Sheets

FIG. 4

| SAMPLE# | SIGNAL | SAMPLE# | SIGNAL |
|---|---|---|---|
| 01 | EKG LEAD I MSB | 02 | EKG LEAD I LSB |
| 03 | EKG LEAD II MSB** | 04 | OTHER |
| 05 | EKG LEAD II LSB | 06 | EKG LEAD III MSB |
| 07 | EKG LEAD III LSB | 08 | OTHER* |
| 09 | EKG LEAD VI MSB | 10 | EKG LEAD VI LSB |
| 11 | EKG LEAD V2 MSB | 12 | OTHER |
| 13 | EKG LEAD V2 LSB | 14 | EKG LEAD V3 MSB |
| 15 | EKG LEAD V3 LSB | 16 | OTHER |
| 17 | EKG LEAD V4 MSB | 13 | EKG LEAD V4 LSB |
| 19 | EKG LEAD V5 MSB | 20 | OTHER |
| 21 | EKG LEAD V5 LSB | 22 | EKG LEAD V6 MSB |
| 23 | EKG LEAD V6 LSB | 24 | OTHER |
| 25 | EKG NEUTRAL MSB | 26 | EKG NEUTRAL LSB |
| 27 | SPO2RED MSB*** | 28 | OTHER |
| 29 | SPO2RED LBS*** | 30 | SPO2 IR MSB*** |
| 31 | SPO2 IR LSB*** | 32 | OTHER |

FIG. 6

SYNCRONIZING A DATA ACQUISITION DEVICE WITH A HOST

FIELD OF THE INVENTION

This invention relates to a method and apparatus for synchronizing data transfer between a data acquisition device that develops data, and a host system that requests the data samples.

BACKGROUND OF THE INVENTION

Various techniques exist to accomplish synchronization for data transfer between a data acquisition device and a host system. However, many of these techniques require significant amounts of hardware and/or software to achieve synchronization. Additional factors to consider are the characteristics of the A/D converter utilized in the acquisition device. In the embodiment illustrated for the present invention, A/D converters are utilized in an electrocardiography (EKG) pod. In this context, the term "pod" refers to a data acquisition device coupled to a medical patient for acquiring EKG signals from the patient, and the term "host" refers to a signal processing and display device which is remote from the pod and forms the remainder portion of a physiological signal patient monitor.

It would be desirable to use sigma-delta A/D converters in the pod to acquire and sample the EKG signals because they have several desirable characteristics: high resolution can be achieved with relatively low cost as compared to sample and hold A/D converters, sigma-delta A/D converters have built in filtering that can reduce 50–60 Hz noise, as well as provide low-pass filtering of the input signal. Furthermore, by choosing the appropriate A/D clock input, any sample rate can be achieved. Additionally, since the A/D converter sample update rate is controlled completely by the A/D clock and not by external data requests, as is the case with a sample and hold A/D converter, sample-to-sample jitter is eliminated.

However, sigma-delta A/D converters have some operating characteristics that need consideration in order that a host system can properly acquire data from them.

Sigma-delta A/D converters are free running, and therefore provide samples at a rate defined by the A/D clock signal. If this clock signal is not derived from the same clock associated with the host system, the rate at which the A/D converter supplies samples will not be the same as the rate at which the host system requests the samples. Samples supplied to the host will be either lost or repeated, depending upon which part of the system has a faster clock. Additionally, when the A/D samples are representative of a sequence of a plurality of different signals whose samples are periodically provided (or updated) by the acquisition device, the periodic updating is generally not done at a time that is "aligned" with the sample requests from the host system for those A/D samples.

Considering the rate problem first, if, for example, the host system sample clock is running slightly faster than the A/D sample update clock, occasionally an A/D sample will be repeated because the host input port is acquiring samples faster than the pod A/D converter can provide new ones. Conversely, if the A/D sampling clock is running slightly faster than the host system sample clock, occasionally a sample will be lost because the pod A/D converter will be providing samples faster than the host input port can acquire them.

These lost or repeated samples result in a discontinuity in the sampled waveform of the acquired signals, e.g., EKG signals. The discontinuity creates added frequency harmonics in the waveform. When software filtering is performed on the acquired waveform, these frequency harmonics may create ringing in the filter output signal. The effects of the ringing and extra frequency harmonics can be reduced somewhat by software changes to the filter characteristics, such as the size of the sampling window and the filter cutoff parameters, but this ringing effect cannot be easily eliminated. Therefore, the filter output waveform has a substantially reduced signal-to-noise ratio, as well as other undesirable characteristics, such as the added harmonics.

One solution to this problem is to allow the host system to sample at a rate slightly faster than the A/D sample update rate. This technique means that occasionally a sample will be repeated. However, if this condition can be detected, the host system can just discard the extra sample and continue. This technique requires special hardware and software to determine that a repeated sample has been read by the host system. This can add cost/complexity to the system, but isn't a significant problem. However, this solution only works well in a system that is data driven, but not in a real-time environment where the host system and acquired data are time driven. In a real-time system, data is being acquired at real time, and even if a repeated sample is detected and discarded, a "hole" in time occurs, and a discontinuity will result. Thus, this technique is not suitable for a real-time data acquisition system such as a patient monitor.

Alternatively, clock synchronization can be achieved by using the same master clock for both the A/D converter in the pod and the pod communication interface to the host. However, this technique may not be available, for example, if the frequency requirements for the pod interface and the A/D converters are different. Secondly, provisions must be made to transmit the host clock frequency to the pod. Any provisions to add a clock signal conductor will undesirably add cost to the system because extra wires and isolation will have to be added to the cable/connector between the pod and the host system.

A second method for synchronizing the two non-synchronous clocks is to employ a conventional phase-locked loop (PLL) arrangement, well known by those of ordinary skill in this technology, wherein one clock signal is used as a master clock, and the other clock signal is produced by applying the DC output signal of the PLL to a voltage controlled oscillator (VCO). The VCO produces an output signal that is frequency locked to the master clock signal. Although PLL components are commercially available, but are expensive, have significant power requirements, and utilize significant circuit board area, all factors which may adversely affect the pod design.

It would be desirable to eliminate the difficulties presented by this synchronization error by providing a method to synchronize the rate of a host system clock with the A/D sampling clock of a remote data acquisition device that provides sampled data to the host system.

The second problem, as previously noted, is to synchronize or "align" the timing of the A/D converter sample updates, so that a given A/D sample of a sequence of a plurality of samples that are developed by the A/D converter is provided to the data communication link at exactly the same time at which the host system requests the given A/D sample, a so-called "just-in-time" data transfer technique. Without such alignment the pod would require data storage, such as a buffer memory, to hold the plurality of samples until they are requested by the host. Addition of such data storage to the pod is undesirable because it increases the size, weight, and power consumption of the pod.

Alignment of host system sample requests with a given A/D sample from the pod can be accomplished, for example, by using an interrupt to signal the host system when the requested sample is ready. However, this technique cannot be used in a system that is not tightly coupled. Where the link between the remote pod and the host system is via a serial interface, the host system is not tightly coupled to the remote pod A/D converter. If the host microprocessor is not tightly coupled to the pod, there will be some latency (delay) associated with when the interrupt occurs vs. when the host microprocessor can actually read the sample from the A/D. Thus, unless the host can immediately request and receive the sample from the A/D when it is ready, e.g., the A/D converter output is directly readable by the host icroprocessor via a simple read instruction, then it can ake a while before the host can actually request the sample indicated as ready and respond to the interrupt. Due to this latency it is highly likely that by the time the host responds to the interrupt and actually reads the sample, the next sample from the A/D is ready, and alignment will be lost. An additional disadvantage of an interrupt driven system is that the host system must respond immediately to the interrupt or the sample update will be lost. This can burden the host system to the point that it prevents the host system from performing other vital real-time tasks.

Alternatively, the host system can poll the A/D system in the pod (e.g., look for a "ready" flag) to determine when the A/D samples are ready, and then request the data. A polling technique also has several drawbacks. Firstly, a significant burden is placed on the host to periodically poll the pod to determine when the samples are ready. This polling technique requires so much processing in a real-time system that it is only effective at very low sample rates. Secondly, there is always a lag between when the A/D system indicates a sample is ready versus when the host system actually requests the data. If this lag becomes too great, A/D samples will be lost because the host does not have time to read all of the A/D data before the next A/D sample update occurs.

The host system can try to align its requests for the A/D samples with when the A/D samples are developed and ready for being provided to the communication link. This technique works well if the A/D samples are occurring at regular intervals. However, this technique significantly increases the amount of processor overhead required by the host to determine when to start the A/D converters, then poll the A/D's at a high rate to determine when a given A/D sample is ready, and finally to "lock onto the A/D samples" in order to align the host's sample requests with when the remote pod's A/D samples are ready. This software based "locking and aligning" technique is further complicated by the fact that the only method of polling a remote pod is via it's communication link, which may be a bandwidth limited serial link, thereby making it difficult to determine precisely when the remote A/D converters produced a sample. Thus, there will be an ambiguity between when a given A/D sample is actually developed, and when the host system will be able to check the A/D ready flag. This ambiguity could result in a lost sample unless special considerations are taken.

Alternatively, a FIFO shift register or buffer can be added to the system. This technique allows the A/D converter in the pod to load the FIFO with the newly developed, i.e., updated, samples, and allows the host system to read these samples when it is ready. This technique does not require the host system requests for reading an A/D sample to be exactly aligned with when each A/D sample update occurs. No data will be lost as long as the host system reads the data at least as fast as the remote pod A/D sample updates occur. Although this technique works well, it results in a significant hardware cost increase for the hardware interface.

All of the above techniques can be used to align the remote pod sample updates with the host system requests, but none are optimal. Each technique either adds complexity to the host system hardware interface and/or its software in order to align the samples.

It would be desirable to synchronize the A/D sample updates to exactly correspond in time with the host sample requests, a kind of "just in time" technique, with minimum increase in complexity of either of the system hardware or software.

Finally, once the host/pod system is locked, data will be properly acquired from the remote pod by the host system. However, the above-described "locking and aligning" techniques require that the sample requests being received from the host system via the serial link are valid.

In any remote system connected via a communications link, the possibility exists that the integrity of the link will be broken. An invalid or lost sample request signal would result in missed A/D samples. Additionally, it is possible that the sample update rate of the A/D converters could change, or even fail completely. In these situations, it is essential that the failure mode be detected so the host system is notified of the error, and can then recover.

It would be desirable to provide a simple mechanism that would recognize an error condition after synchronization has been established, and upon such recognition, re-establish synchronization with a minimum increase in complexity of either of the system hardware or software.

SUMMARY OF THE INVENTION

In the present invention a data acquisition pod including a signal sampling A/D converter is coupled to a host system via a data communication link. A hardware technique is provided in the pod for synchronizing a reference clock signal received from the host system with a clock signal in the data acquisition pod that operates the A/D converter, so that the A/D converter provides a plurality of samples to the data communication link at exactly the same rate as the rate at which the host system requests the samples. Thus, neither hardware nor software provisions have to be made to take into account lost or repeated samples due to a difference in sample rate between the A/D converter and the host system. Additionally, a given A/D sample of a sequence of a plurality of samples that are developed by the A/D converter is provided to the data communication link by the A/D converter in a manner that is "aligned in time" to occur at exactly the same time at which the host system requests the given A/D sample. Thus, provisions do not have to be made to store the plurality of the A/D samples until the host system is ready to start receiving them.

More specifically, in a preferred embodiment of the invention the data acquisition pod includes a decoder having an input coupled to the data communication link and responsive to a plurality of sample requests from the host system for extracting a host reference signal having a host reference frequency. The pod includes an A/D converter of the oversampling type (such as a sigma-delta converter), and a clock signal source for developing an A/D reference clock signal having a frequency that is different from the host reference frequency by a predetermined amount. A pulse modifying digital phase-locked loop (PLL) is responsive to the A/D reference clock signal and the host reference signal for developing an A/D clock signal in which one of its clock periods is periodically modified, thereby locking the rate at which the A/D converter develops samples to the rate at which the host system requests samples. Additionally, the pod includes a signal detector responsive to a specified alignment in time of a given sample of a sequence of a plurality of samples that are developed by the A/D converter with a host system request for that given sample, for selectively providing an enable signal to the digital (PLL). By only providing the enable signal to the digital PLL after detecting the specified alignment, before the PLL is enabled the A/D converter samples are developed at a rate which allows the development of the given A/D sample to "slide in time" with respect to the request for that sample by the host system. Once the signal detector indicates that the given sample is developed at a time that is precisely aligned with the host system request for that given sample, the PLL is enabled, thereby synchronizing and locking the providing to the communication link of the plurality of samples developed by the A/D converter with the host system requests for those samples.

By using a digital phase-locked loop a very low cost method for both synchronizing and aligning the data transfer between the remote pod and the host system is achieved. Although the stretched clock pulse from the digital phase locked loop causes a discontinuity of the waveform being sampled by the sigma-delta A/D converter as it performs a conversion, since the sigma- delta A/D converter samples at such a high clock rate, and then heavily filters and decimates the oversampled signal, the noise and discontinuity caused thereby is spread across a wide frequency range. This frequency spreading of the noise necessarily reduces the noise in the narrower bandwidth of the desired signals of interest to a minimal amount. Additionally, any noise spikes produced by the discontinuity are outside the frequency range of interest. Thus, any noise produced by the discontinuity, and filter ringing effects due to the pulse stretching, is minimized, and does not adversely effect the overall accuracy and signal-to-noise ratio of the system.

In accordance with a further aspect of the invention, the host system sample requests from the pod are monitored for error detection. Upon detection of an error, the pod hardware utilizes the synchronization locking and alignment techniques described above to selectively enable and disable A/D clock slipping between the two systems, thereby providing a simple and cost effective method of error recovery.

BRIEF DESCRIPTION OF THE DRAWINGS

FIG. 4 illustrates a table of sample order for the data transfer from the data acquisition device to the host monitor of FIG. 1.

FIG. 6 illustrates a timing diagram useful for understanding the synchronization and alignment of the data transfer from the data acquisition device and the host monitor of FIG. 1.

DETAILED DESCRIPTION OF INVENTION

The present invention will now be described in conjunction with an exemplary embodiment of an apparatus for monitoring vital signs of a medical patient. One example of a monitor apparatus is described in U.S. Pat. No. 5,375,604 (Kelly et al.) issued on Dec. 27, 1994 and assigned to Siemens Medical Electronics, Inc., incorporated herein by reference. The apparatus includes a remote data acquisition device (referred to hereinafter as an EKG pod), and a patient monitor (referred to hereinafter as a host) which is connected to the EKG pod.

Figure 1:
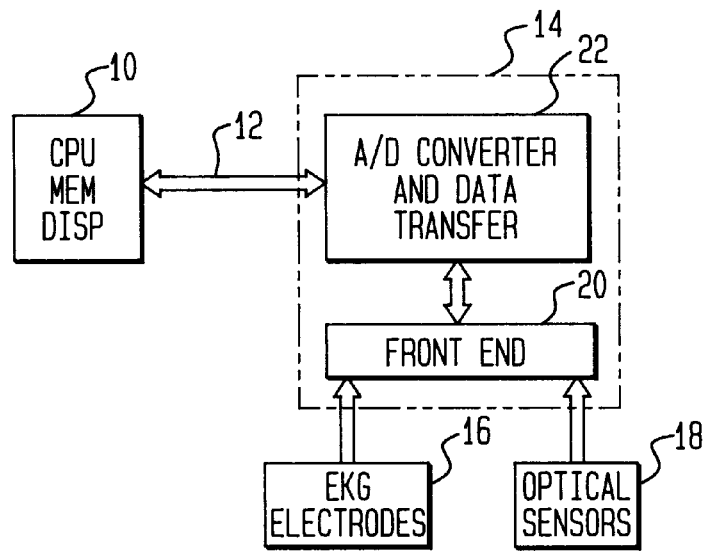
FIG. 1 is a functional block diagram of a remote data acquisition device and a host system that operates in accordance with the principles of the present invention.

As shown in FIG. 1 a host patient monitor 10 includes a central processing unit (CPU), memory (MEM) and display (DISP) that is coupled via a communication link 12 to an EKG pod 14. Pod 14 is advantageously embodied in a relatively small housing so that it may be placed with relative ease in close proximity to a medical patient (not shown). A plurality of physiological signal sensors, such as a plurality of EKG electrodes 16 for sensing electrocardiographic signals and optical sensors 18 for sensing blood oxygen levels ($SpO_2$), are coupled to the patient for providing analog vital sign signals to a front-end portion 20 of pod 14. As well known by those of ordinary skill in this technology, and as described in greater detail in the forenoted U.S. Patent by Kelly et al., the above-described apparatus comprise a patient vital sign monitor.

More specifically, front-end portion 20 includes filter and amplifier circuits for removing noise and other undesirable signals which physiological sensors 16 and 18 may acquire. The filtered and amplified signals are then digitized and prepared for transfer to the host patient monitor 10 by an A/D converter and data transfer interface portion 22 of pod 14, and then transferred to monitor 10 via communication link 12. In monitor 10 the digitized physiological data are processed by the CPU for developing EKG waveforms and possibly QRS, arrhythmia and ST segment analysis. The processed information is subsequently displayed on the display of monitor 10 along with a display of the blood oxygen levels acquired by sensors 18. It should be noted that further physiological parameters could also be sensed from the patient and processed and displayed in a manner similar to the processing and display of the physiological parameters previously described. The patient monitoring system described so far is substantially similar to that described in the forenoted U.S. Patent to Kelly et al., however, in the Kelly patent there is no specific description concerning synchronization of the clock signals used for processing and transferring the acquired data and control commands between the patient monitor and the pod. One obvious way to provide synchronization is to have extra wires in the communication interface between monitor 10 and pod 14, in order to transmit the host clock to the pod. However, as noted in the background portion of this application, such provision will add cost to this system, as well as undesirably increase the size of the cable/connectors used in the communication interface, as well as other problems relating to providing a stable synchronization between monitor 10 and pod 14.

Figure 2:
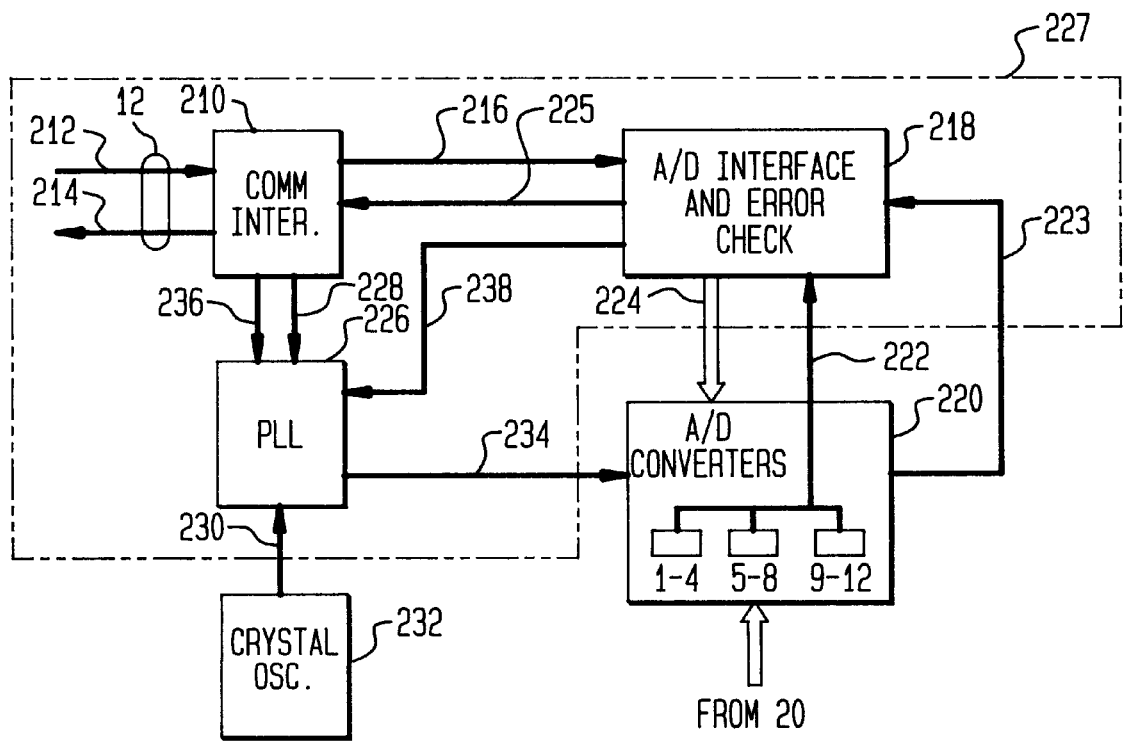
FIG. 2 illustrates details of the digitization and data transfer portion of the embodiment shown in FIG. 1.

FIG. 2 illustrates details of the digitization and data transfer portion 22 of pod 14. As shown therein, digitizer 22 includes a communication interface 210 having an input 212 for receiving a serial stream of digital commands from host monitor 10 and providing at lead 214 a serial stream of digital data acquired by pod 14 and representative of the physiological parameters monitored from the patient, as well as status and other administrative information necessary for operating the patient monitoring system. Communication interface 210 may comprise any one of various types of programmable logic devices or field programmable arrays for functioning according to a given established data transfer protocol or format for coding/decoding and transferring of information between monitor 10 and pod 14. In the preferred embodiment, communication interface 210 comprises an Application Specific Integrated Circuit (commonly referred to as an ASIC), constructed using, for example a field programmable gate array, programmed to operate as a state machine for accomplishing its function.

Figure 3:
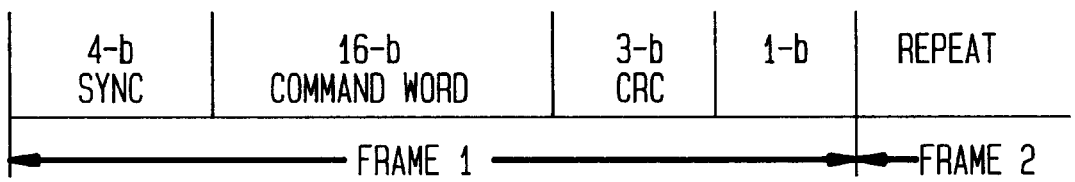
FIG. 3 illustrates the data transfer format used for data transfer from the host monitor to the data acquisition device of FIG. 1.

The format protocol for the communication from monitor 10 to pod 14 is shown generally in FIG. 3, and comprises a serial sequence of frames, F1, F2, etc. Each frame begins with a 4-bit synchronizing word comprising a unique sequence of bits for indicating the beginning of a frame, commonly referred to as a header. The next 16 bits are used for indicating a command, such as a request for A/D sample data, status information, or identification of pod 14, etc. The first 4 of these 16 bits may be used to identify a type of command, and the remainder of the bits may be used to identify a more particular request within that command. For example, the command word may be "request A/D sample data", and the more particular request could be "from A/D converter 22". The last 3 bits of the frame are used for providing a CRC error checking code. The next frame starts after a gap having a width of 1 bit, resulting in 24 bits for each frame. A Manchester encoder/decoder, as well known by those of ordinary skill in this technology, can be used at the communication interfaces of communication link 12 for the coding and decoding of the data and commands.

Communication interface 210 translates the commands received at input 212 into requests for data which are applied at lead 216 to an A/D interface 218. An A/D converter arrangement 220 is responsive to the analog physiological signals provided from front end 20 for developing a serial stream of digital data representative of a predetermined sequence of digitized samples of the analog signals, and provides these digital data samples to A/D interface 218 via a data path 222, as well as an A/D ready signal on path 223 that indicates when the A/D converters of arrangement 220 have completed their acquisition of the digital data samples and the digital data is ready to be provided. A/D interface 218 also provides read requests (strobes) to A/D converter arrangement 220 via a data path 224 for initiating their providing of the digital data samples to interface 218. The data signals are applied from interface 218 to communication interface 210 via data path 225. In the preferred embodiment, A/D interface 218 also comprises an ASIC, and also operates as a state machine for accomplishing its function.

In the present invention, the A/D converters of arrangement 220 are of the sigma-delta type for digitizing the physiological signals provided to it by front end 20. As shown in exemplary embodiment of FIG. 2, there are three groups of four sigma-delta A/D converters, a first group $220_{1-4}$, a second group $220_{5-8}$, and a third group $220_{9-12}$, providing a total of twelve channels of digitized sample data. Ten of these data channels are used to sample EKG leads I-III, V1 to V6 and neutral, while the remaining two channels are used to sample the RED and INFRARED signals provide by $SpO_2$ sensors 18. As well known, each sigma delta A/D converter digitizes a sample of the analog signal at a very high rate, developing a serial stream of bits, that are then filtered and decimated to develop a multi-bit digital sample at a lower rate. In the exemplary embodiment, 22-bit digital samples for each analog signal are developed at a 2 kHz rate using 3 A/D converter IC chips (of the type manufactured and commercially available by Analog Devices under part number AD 7716) that have their outputs daisy-chained together for serial output clocking of the A/D data, thus forming A/D converter arrangement 220.

Since the digitized sample data are sent to monitor 10 serially, with successive samples of each of the analog signals being updated in pod 14 at the 2 kHz rate, i.e., each 500 microseconds ($\mu$s), the 12 channels of data provided by sigma-delta A/D converters $220_{1-12}$ are provided in a predetermined sequence. Thus, each 500 $\mu$s it is necessary that host monitor 10 not only receive all of the current digital sample data for each of the 12 physiological signals that are sent from pod 14, establishing the need for a means for clock synchronization, but host monitor 10 must also know the signal sequence that the A/D digital data represents.

More specifically, each 500 $\mu$s one of each of the twelve A/D data converter samples are selected by host monitor 10 via an "EKG SIGNAL SELECTION" command word, as shown in FIG. 3, which commands should request A/D sample data in an order that exactly matches the predetermined hardwired connections that determine the order that these signals are provided to communication link 12 by interfaces 218 and 210. FIG. 4 illustrates one example of a sample request table that is generated by host monitor 10. Basically, there are 32 time slots appearing at a 2 kHz rate that are used for transfer of data from pod 14 to monitor 10. Further details of the sample table will be provided later. If any A/D data for a particular converter is requested out of the defined sequence, the wrong A/D data will be obtained by monitor 10, resulting in grossly inaccurate patient monitoring.

Pod 14 includes means for monitoring the sample requests from monitor 10, and if an incorrect sequence of requests is detected (because of noise in communication link 12, or some other malfunction), communication interface 210 will set an error status flag on signal path 236, which will be used as described in more detail later for re-establishing clock synchronization between monitor 10 and pod 14.

Since host monitor 10 sets up the sample request table in its memory, and in the exemplary embodiment the sample table is updated/looked at every 640 samples, or 10 msec., there is no easy way for pod 14 to quickly interrupt monitor 10 in the event it detects an error, i.e., it is not tightly coupled to pod 14. Even if there was a way to generate the interrupt, monitor 10 can't update the table and make a new request for up to 10 msec. By then many A/D samples have passed and alignment with the transmitted samples will be lost. Thus, provision must be made for aligning the sequence of sampled data provided by pod 14 to the sequence that the data is requested by host monitor 10. However, before description of how the alignment problem is solved by the present invention, the description and solution to the problem of sample rate synchronization between the host and pod will first be described.

Ideally, the bandwidth of link 12 allows it to acquire, for example, exactly 32 16-bit words each 500 $\mu$s period (resulting in a link sample rate of 64 kHz). Since, as previously noted, each A/D sample is 22 bits, with status information it becomes 32 bits. Thus, 24 of the 32 bit words will be used for A/D data, and the remaining 8 of the 32 words can be used for status and other information. Thus, if the system is frequency locked, every 500 $\mu$s, one sample from each of the A/D converters is sent from pod 14 to the monitor 10 via link 12, along with status information, and then the A/D converters are updated with the digital sample data in preparation for transmission to host 10 of the next group of 24 A/D samples.

Realistically, however, link 12 actually acquires data at 64 khz +/− a clock tolerance, and the A/D converter's are producing samples at 2 khz +/− a clock tolerance. Thus, there will be a "sample slip" if these two tolerances do not exactly match.

If the clock of monitor 10 is running slightly faster than the clock controlling A/D converter 220, occasionally an A/D sample will be repeated because monitor 10 is acquiring samples from link 12 faster than A/D converter 220 can provide them. Conversely, if the A/D sampling clock is running slightly faster than the monitor clock, then occasionally a sample will be lost, because the A/D converters will be providing samples faster than monitor 10 can acquire them.

This lost or repeated sample results in a discontinuity in the sampled waveform of the acquired EKG signals. The discontinuity creates added frequency harmonics in the waveform. When software filtering is performed on the acquired waveform, these frequency harmonics may create ringing in the output of the filtered. The ringing and extra frequency harmonics can be modified somewhat by changing characteristics of the software filter, such as the size of the sampling window and the filter cutoff parameters, but this ringing effect cannot be easily eliminated. Therefore, the resultant filtered waveform has a substantially reduced signal-to-noise ratio, as well as other undesirable characteristics, such as the added harmonics.

In accordance with one aspect of the present invention, for synchronizing the providing of the sampled A/D data with the monitor requests for that sampled A/D data, a pulse modifying digital phase locked loop arrangement (PLL) 226 is provided. PLL 226 is designed to minimize gate count yet provide a method to "lock" the rate of clock signal that operates the A/D converter in pod 14 to the data rate of monitor 10 and link 12. PLL 226 may also be formed from an ASIC, and in the preferred embodiment, PLL 226 is formed on the same ASIC that is used to form interfaces 210 and 218, as indicted in FIG. 2 by dashed line 227.

In general, PLL 226 receives at a first input a host reference signal 228, and receives at a second input an A/D reference clock signal 230. The A/D reference clock signal 230 is generated by a crystal oscillator 232.

Host reference signal 228 is derived by interface 210 decoding the sync portion of each of the successive Frames received from monitor 10 over link 12. As previously noted, host monitor 10 has a 64 kHz sample rate, so the frequency of host reference signal 228 is 64 kHz. Crystal oscillator 232 sets the frequency of reference clock signal 230 so that after division by a counter arrangement at the input of PLL 226, the divided down signal is slightly higher than the frequency of host reference signal 228. PLL 226 develops an A/D clock signal 234 that is synchronized with the frequency of host reference signal 228, and applied to A/D converters 220 for controlling its digitization rate, as well known. Additionally, PLL disable signals 236 and 238 are provided to PLL 226 from interfaces 210 and 218, respectively, and will be described in greater detail later.

Figure 5:
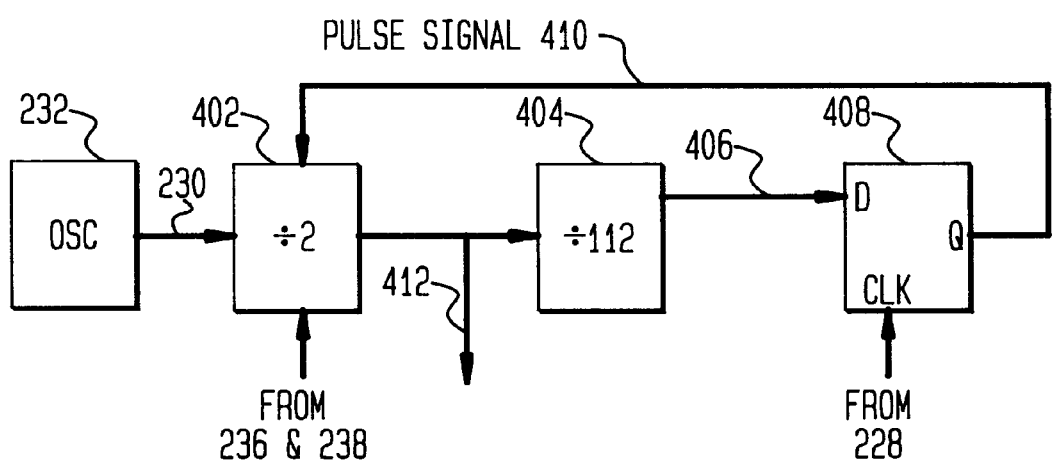
FIG. 5 illustrates details of the PLL portion of FIG. 2.

FIG. 5 illustrates in block diagram form details of PLL 226, which operates in a manner as described in an Application Note published by Actel Corporation in April 1996 entitled "Using FPGAs for Digital PLL Applications". As described therein, and as shown in FIG. 5, in the exemplary embodiment PLL 226 is of the "pulse stealing" type. It includes a two-stage divider at its input, in the exemplary embodiment comprising a ÷2 counter 402 followed by a ÷112 counter 404. The two-stage divider receives at its input the "slightly higher" reference clock frequency signal 230, and after division applies a divided-down (64$^+$ kHz) signal 406 to the "D" input of a flip-flop detector 408. The 64 kHz host reference signal 228 is applied to the "CLK" (clock) input of detector 408. When the rising edge of signal 406 at the D input of detector 408 precedes the arrival time of the rising edge of signal 228 at the CLK input of detector 408, the Q output of detector 408 goes high, providing a pulse signal 410 that is applied as a "disable" input to counter 402. In response, counter 402 stops its counting of A/D reference clock signal 230 for one period of its input clock. This disabling effectively stretches its counting action by one clock period, and apparently "stealing" one of its input clock pulses. Consequently, at a time just after the pulse stealing, the arrival time at detector 408 of the next pulse of signal 406 will lag the arrival time of the next pulse of the host reference signal 228. However, since the frequency of the A/D reference clock signal 230 is set so that the frequency of the divided-down signal 406 is slightly higher (64$^+$ kHz) than the 64 kHz host reference signal 228, the rising edge of the successive pulses of signal 406 will slowly "slip ahead in time" with respect to the pulses of signal 228, until the Q output of detector 408 again goes high, providing a further disabling pulse on signal 410 and causing a further pulse stealing. This process periodically repeats, in the average resulting in a frequency locked relationship between an output signal 412 from divider 402 and the 64 kHz host reference signal 228. Output signal 412 is then be used as the A/D clock signal (234 of FIG. 2) for A/D converters 220 so that its A/D sample rate will be synchronized with the read rate of host monitor 10. In the exemplary embodiment, the frequency of the A/D reference clock signal 230 is 14.368 mHz, and since the frequency of host reference signal 228 is 64 kHz, the average frequency of the actual A/D clock signal 412 turns out to be 7.168 mHz (note: 7.168 mHz ÷112 is exactly 64 kHz).

These chosen frequencies for signal 230, signal 228 and the divider values, cause signal 406 to slip 34.8 ns for every 64 kHz pulse of signal 228. The 34.8 ns. slip equals approximately one/half of the period of the 14.368 mHz signal 230 (1/14.368 mhz=69.599 ns.). Thus every other period of signal 228, the pulses of signal 406 will have slipped just ahead of the pulses of signal 228. Counter 402 will delay one clock period of signal 230, and pulses of signal 228 will slip back ahead of pulses of signal 406 by 69.599 ns. This cycle repeats approximately every other period of signal 228, i.e., at a 32 khz rate, resulting in the forenoted desired 14.336 mhz average frequency for signal 234.

The pulse stealing of the A/D input clock does have an effect on the A/D converter's cutoff frequency, output settling time, and other filter characteristics. However, each A/D sample is 14*2*256=7,168 clocks per sample. Thus, the total percent of "stretched" clock periods is 16/7168=0.22%, which is a relatively insignificant number.

Although the stolen pulse causes a discontinuity (noise) in the sampled waveform, it is also relatively insignificant. Since the sigma-delta A/D converter has such a relatively high sample rate, and heavily filters and decimates the oversampled signal to the 2 khz output sample rate, the noise generated by the discontinuity is spread across a wide frequency range, which effectively reduces the noise in the desired 2 khz bandwidth to a minimal amount. Consequently, noise produced by the pulse stealing is minimized, and does not adversely effect the overall accuracy and signal to noise ratio of the system.

Note that although in the exemplary embodiment PLL 226 is of the "pulse stealing" type, because the frequency of the pod clock signal is set to be slightly higher than the frequency of the derived host clock signal, a "pulse adding" type of PLL could also be used. In this case the frequency of the pod clock signal would be set to be slightly lower than the frequency of the derived host clock signal. Furthermore, although in the exemplary embodiment sigma delta A/D converters are used, in fact any "oversampling" type of A/D converter would be useful. Thus, in the present invention, a "pulse modifying" PLL in combination with an oversampling type of A/D converter is used.

As previously noted, aside from clock synchronization, another constraint exists: since the A/D converter channels are daisy chained together, each sample provided from the A/D converters corresponds to how the A/D converters are connected, and that order must exactly match the specific sample order requested by monitor 10 in via the sample table of FIG. 4. The physical connections of converter 220 requires that the data of the A/D converters of group 1–4 are sequentially clocked out first, followed by the data of A/D converters 5–8, and finally A/D converters 9–12. In order to properly align the A/D data with the sample requests from monitor 10, it is necessary that the order match the sample requests of the sample table shown by FIG. 4.

Thus, means must be provided to prevent the A/D converters from updating their outputs to the next sample value (which occurs each 500 μs), during the time monitor 10 is acquiring the previous 12 channels of A/D samples. As previously noted, much of the bandwidth of link 12 is consumed with clocking the data out of the A/D converters (24 of the 32 samples within 500 μsec.) and sending the requested data from pod 14 to the monitor 10. Unless the updating of the A/D samples are locked to occur at a specified alignment in time, it is very likely that the A/D sample data updates will prevent proper transfer of all of the A/D samples of the preceding 500 μs period from being transferred to monitor 10.

Various known techniques can be used. One common technique is to "double buffer" the A/D data by clocking out the A/D samples each time a sample update occurs, and placing the data in a FIFO buffer or other memory device until monitor 10 requests the samples. Then, as the monitor is reading the A/D data from the FIFO, the next A/D sample update can occur and be loaded into the FIFO as the next group of A,/D samples to be read. This technique of filling the FIFO with the A/D samples as they are ready, and emptying the FIFO as the samples are requested, allows the A/D converter sample update to occur asynchronously to monitor sample requests.

Although FIFO's, and other types of buffers, such as a ping-pong buffer in RAM memory, allows the A/D samples to be generated asynchronous to the requests, there is added cost and complexity associated therewith. A more desirable technique would be to synchronize or time the A/D sample updates to correspond exactly with the requests for those samples by the monitor.

Such a synchronization technique would allow the monitor to read the 12 channels of updated A/D samples as they occur, a kind of just-in-time technique. Then, shortly after all samples have been read, the next A/D update occurs, and the process repeats. In order for this technique to work, two conditions are required:

1. The A/D sample rate must be locked to the monitor clock rate. This is achieved with the digital PLL 226 described above, and
2. The A/D sample updates must align with the monitor sample requests. Ideally, the A/D sample update occurs, interfaces 218 and 210 acquire and transmit all the data, and then shortly afterwards, the next A/D sample update occurs.

FIG. 6 illustrates this alignment for the updating of the A/D samples vs. the requests for these samples. As shown, updating does not occur during the monitor requests for the 12 channels of EKG sample data.

In accordance with a further aspect of the present invention, the technique used to align and then lock the required synchronization of the monitor sample requests with the providing by pod 14 of the updated A/D samples takes advantage of the "slipping" between the 64 kHz monitor reference signal 228 and the A/D clock signal 234, which slipping occurs until digital PLL 226 is enabled. PLL 226 is enabled by the level of enable/disable signals 236 and 238 applied to its enable input. Before the "lock" occurs, 32 sample time slots occur in the link communication path every 500 μs, but since the divided down A/D clock signal 406 is slightly faster than the monitor reference signal 228, the time when the A/D sample update period occurs is "slipping" through the 500 μs communication window. Thus, the logic embedded in the ASIC comprising interface 218 does not initially enable PLL 226, and instead initially allows "slipping" to occur.

A detection circuit (not shown) in interface 218 monitors and decodes the sample requests from the command words received from monitor 10 over link 12. The detection circuit also monitors the A/D READY signal 223 indicating that each of the 3 groups of A/D converters 220 have finished updating. The detection circuit determines that the A/D converter updating has "slipped" into the proper place within the 500 μsec window (as shown by FIG. 6), by checking when the received sample requests occur relative to the occurrence of the A/D READY signal 223. When the A/D sample update has slipped into the place as shown in FIG. 6, the detection circuit causes signal 238 to have a level that immediately enables the PLL 226, and thereafter the A/D sample updates will no longer be "slipping" with respect to the 64 khz monitor sample rate. From this point forward, both monitor 10 and pod 14 are locked and synchronized.

To function properly, all 12 of the A/D converters must be synchronized and updating at exactly the same rate. Interface 218 contains circuitry that allows proper initialization of the A/D converters. On a power-up condition, interface 218 holds all 12 A/D converters 220 in reset. After monitor 10 sets up the sample table shown in FIG. 4, a command word will be sent by monitor 10 to pod 14 indicating A/D ENABLE. The A/D ENABLE word can be sent as one of the OTHER of the 32 time slots indicated in the table of FIG. 4. Upon receipt of this command word, interface 218 simultaneously releases all 12 of A/D converters 220 from reset. From this point forward, all of A/D converters 220 will be simultaneously sampling each of their respective analog input signals at the 2 khz rate.

To minimize the time needed for synchronization, the A/D ENABLE word should be sent just after monitor 10 has made a request for the last A/D sample. Location 31 in the table is the last A/D sample request, however in the exemplary embodiment there is the three frame processing delay associated with the communication link 12. Thus the actual response for the last A/D sample is three frames later, or location 2 in the FIG. 4. Thus the ideal location to send the CONTROL COMMAND for A/D ENABLE is at location 8.

Placing the A/D ENABLE command in location 8 allows A/D converters 220 enough time to stabilize before the clock synchronization circuitry of PLL 226 becomes activated. In general, the sliding of the "update" window (as described above) will be activated after the A/D sample update has "slipped" about 5 Frames, or about 78 μs. This translates into about 1080 clock periods. Since the clock period is about 70 ns (1/14.368 mhz), and the slip rate is 32 clocks per msec (see calculations above), the total time required for a "locked" condition is: 1080 clocks/(32 clocks per m sec)=34 msec. Hence, if the A/D ENABLE command is placed in location 8, the hardware will obtain a "locked and synchronized" condition 34 msec. after the A/D converters are enabled by the A/D ENABLE command.

Once the monitor/pod clocks are "LOCKED AND SYNCHRONIZED", various conditions can cause them to loose this state. For example, a lost A/D sample due to noise on link 12 (e.g., during cautery surgery) could cause a loss of clock frequency synchronization, or an A/D sequence error. Furthermore, a random glitch or glitches on the A/D clock will cause a shift between update of the A/D samples and the sequence for the requests for those samples. A lost A/D clock could also mis-align the sampled data with the requests. It is even possible for one of the 12 of A/D's to become unsynchronized with the others.

As previously noted, it is necessary to recover from such error conditions in the event that the system becomes unlocked, unaligned, or unsynchronized. Consequently, interface ASIC's 210 and 218 contain logic circuity (configured as a state machine, well known by those of ordinary skill in this technology) that provides for error checking and error recovery. For example, if any of A/D READY signals 223 of the 3 groups of A/D converters 220 drift outside the UPDATE window indicated in FIG. 6, interface 218 will immediately sense an "unaligned" condition and apply an error signal 238 to PLL 226, and also advise monitor 10 via setting of error flags in the EKG STATUS word portion of the format shown in FIG. 3, in an attempt to re-align the system. Monitor 10 software will monitor these flags, which will stay set until the system re-aligns.

Additionally, if any sample request received by interface 210 does not match the exact sequence specified by the table of FIG. 4, interface 210 will apply an error signal 236 to PLL 226.

Once an error is detected, in response to signals 236 or 238, the pulse stealing by digital PLL 226 will become disabled so that synchronization of the A/D converter clock will become unlocked with respect to the host system reference signal. The host system software processes the error status flag for error reporting and logging. Additionally, the software checks to determine if a predetermined number of errors have been exceeded in a given period, and if so, the operating power to the pod will be cycled in an "last ditch" attempt to remove the error condition. The system will remain unlocked and clock "slipping" between the host reference signal and the A/D clock signal will resume until the signal detection circuitry in interface 210 again detects the specified alignment between a given host sample request and the providing by A/D converter 220 of that sample.

Under certain conditions, an error may persist. One such case is if one of the A/D ready signals becomes misaligned with respect to the other two A/D ready signals. Since the error detection circuit in interface 218 checks to ensure that each one of the 3 groups of all A/D's are synchronized and the A/D READY signals are aligned, interface 218 will always detect an error condition. In this case, the software of monitor 10 should cycle the A/D ENABLE control flag to reset A/D converters 220.

Thus, there has been shown and described a novel clock synchronization method and apparatus for use by a data acquisition and device which satisfies all the objects and advantages sought. Many changes, modifications, variations and other uses and applications of the subject invention will, however, become apparent to those skilled in the art after considering this specification and its accompanying drawings, which disclose preferred embodiments thereof. For example, as previously noted, although in the illustrated preferred embodiment a pulse stealing PLL is used, a pulse adding PLL could be used. Additionally, it is not necessary that the A/D converter be of the sigma delta type, and in fact other types of oversampling A/D converters may be used.

All such changes, modifications, variations and other uses and applications which do not depart from the invention as described and claimed herein are deemed to be covered by this patent, which is limited only by the claims which follow as interpreted in light of the foregoing description.

We claim:

1. In a data acquisition pod of the type having a signal sampling A/D converter that is coupled to a host system via a data communication link, apparatus for synchronizing a host-derived reference clock signal with a clock signal in the data acquisition pod that operates the A/D converter, so that the A/D converter provides samples to the data communication link at the same rate as the rate at which the host system requests the samples, comprising:

a decoder having an input coupled to the data communication link for extracting from communication received from the host a host reference signal having a host reference frequency;

a clock signal source for developing an A/D reference clock signal having a frequency that is offset a predetermined amount from the frequency of the host reference frequency;

an A/D converter of the oversampling type having an A/D converter clock signal input; and a pulse modifying digital phase-locked loop (PLL) responsive to the A/D reference clock signal and the host reference signal for developing an A/D clock signal in which one of its clock periods is periodically modified, said A/D reference clock signal being coupled to said A/D converter clock signal input, thereby locking the rate at which the A/D converter develops samples to the rate at which the host system requests samples.

2. Apparatus in accordance with claim 1, wherein said decoder, signal detector and said PLL are formed using an ASIC.

3. Apparatus in accordance with claim 1, wherein the decoder is responsive to a plurality of sample requests from the host system for extracting the host reference frequency.

4. Apparatus in accordance with claim 1, wherein the A/D converter is of the sigma-delta type.

5. Apparatus in accordance with claim 1, wherein the frequency of said A/D reference clock signal is slightly greater than the frequency of said host reference signal, and said pulse modifying PLL is a pulse stealing PLL, developing an A/D clock signal in which one of its clock periods is periodically stretched.

6. Apparatus in accordance with claim 1, wherein said A/D converter develops a sequence of a plurality of samples, and said data acquisition pod further includes:

a signal detector responsive to the host system requests for samples and the readiness of the A/D converter to provide those samples for detecting a specified alignment in time of a given sample of said sequence of samples with a host system request for that given sample, and upon such detection, selectively providing an enable signal to the PLL, thereby enabling its pulse modifying operation and locking in a given alignment the providing to the communication link of the plurality of samples developed by the A/D converter with the requests by the host system for those samples.

7. Apparatus in accordance with claim 6, wherein said A/D converter comprises a plurality of A/D converters operating in parallel on a respective one of a corresponding plurality of analog input signals, each A/D converter providing an A/D READY signal to said signal detector for indicating its readiness to provide digital samples.

8. Apparatus in accordance with claim 7, wherein said plurality of A/D converters provide said digital samples as a serial data stream.

9. Apparatus in accordance with claim 6, wherein said data acquisition pod includes error checking circuitry responsive to said sample requests from the host system for examining each sample requests on a sample by sample basis, and if any sample request is missing, out of order from a pre-determined sample order, or becomes un-synchronized with the specified sequence that samples are ready to be provided by the A/D converter, removes the enable signal from the PLL so that the time at which the given sample is ready to be provided by the A/D converter is allowed to slip with respect to the time that the host system requests that given sample.

10. Apparatus in accordance with claim 9, wherein said decoder, signal detector, error checking circuitry and PLL are formed using an ASIC.

11. Apparatus in accordance with claim 9, wherein after removing said enable signal, said error checking circuitry remains responsive to said sample requests from the host system for re-detecting the specified alignment in time of the given sample of the sequence of samples with a host system request for that given sample, and includes means responsive to said re-detection for then re-applying said enable signal to said PLL.

12. A method for synchronizing a reference clock signal that operates a host system with a clock signal developed in a data acquisition pod that operates an A/D converter in the pod, so that the A/D converter provides samples to a data communication link connecting the host and pod at the same rate as the rate at which the host system requests the samples, the method comprising:

decoding communications received over the data communication link from the host system for extracting a host reference signal having a host reference frequency;

providing a clock signal source for an A/D reference clock signal having a frequency that is different from the host reference frequency;

developing a sequence of a plurality of digital samples of at least one analog input signal using an oversampling type of A/D converter having an A/D converter clock signal input; and developing an A/D clock signal that is synchronized with the host reference signal by using a pulse modifying phase-locked loop (PLL) responsive to the A/D reference clock signal and the host reference signal, said PLL causing one of the clock periods of the A/D clock signal to be periodically modified, said A/D reference clock signal being coupled to said A/D converter clock signal input, thereby locking the rate at which the A/D converter develops samples to the rate at which the host system requests samples.

13. The method of claim 12, wherein said decoding step decodes a plurality of sample requests from the host system for extracting the host reference frequency.

14. The method of claim 12, wherein said step of developing a sequence of digital samples uses a sigma delta A/D converter for providing said samples as a serial data stream.

15. The method of claim 12, wherein the frequency of said A/D reference clock signal is slightly greater than the frequency of said host reference signal, and said step of developing an A/D clock signal develops an A/D clock signal in which one of its clock periods is periodically stretched.

16. The method of claim 12, comprising the further step of:

detecting the timing of the host system requests for a sequence of samples and the readiness of the A/D converter to provide those samples, for selectively providing an enable signal to the PLL upon detecting a specified alignment in time of a given sample of sequence of samples with a host system request for that given sample, thereby enabling said PLL pulse modifying operation and locking in a given time alignment the providing to the host of the sequence of samples developed by the A/D converter with the host system requests for those samples.

17. The method of claim 16, wherein said detector step detects an A/D READY signal from a plurality of A/D converters operating in parallel on a respective one of a corresponding plurality of analog input signals, each A/D READY signal indicating its readiness to provide digital samples.

18. The method of claim 12, including the further step of error checking said sample requests from the host system on a sample by sample basis, and if any sample request is missing, out of order from a pre-determined sample order, or becomes un-synchronized with the sequence that samples are ready to be provided by the A/D converter, removes the enable signal from the PLL so that the time at which the given sample is ready to be provided by the A/D converter is allowed to slip with respect to the time that the host system requests that given sample.

19. The method of claim 18, wherein said error checking step, after removing said enable signal, continues to check said sample requests from the host system for re-detecting the specified alignment in time of the given sample of the sequence of samples with a host system request for that given sample, and includes a step for re-applying said enable signal to said PLL upon said re-detection.

* * * * *